(12) United States Patent
Naoum

(10) Patent No.: US 9,730,858 B2
(45) Date of Patent: Aug. 15, 2017

(54) DEVICE OF CONTROLLED PROVISION OF SEA WATER IN THE NOSE

(71) Applicant: George Naoum, Gkizi Attikis (GR)

(72) Inventor: George Naoum, Gkizi Attikis (GR)

(*) Notice: Subject to any disclaimer, the term of this patent is extended or adjusted under 35 U.S.C. 154(b) by 0 days.

(21) Appl. No.: 14/780,072

(22) PCT Filed: Mar. 24, 2014

(86) PCT No.: PCT/GR2014/000020
§ 371 (c)(1),
(2) Date: Sep. 25, 2015

(87) PCT Pub. No.: WO2014/155140
PCT Pub. Date: Oct. 2, 2014

(65) Prior Publication Data
US 2016/0030282 A1   Feb. 4, 2016

(30) Foreign Application Priority Data
Mar. 26, 2013   (GR) .............................. 20130100173

(51) Int. Cl.
*A61M 31/00*   (2006.01)
*A61M 37/00*   (2006.01)
(Continued)

(52) U.S. Cl.
CPC ........... *A61H 35/04* (2013.01); *A61M 3/0279* (2013.01); *A61M 16/06* (2013.01);
(Continued)

(58) Field of Classification Search
CPC .. A61M 2210/0618; A61M 2039/0009; A61H 35/008; A61H 35/04; A61H 2033/043
(Continued)

(56) References Cited

U.S. PATENT DOCUMENTS

| 1,856,811 A | * | 5/1932 | Inaki | ................... A61M 3/0262 |
| | | | | 604/183 |
| 5,921,233 A | * | 7/1999 | Gold | ...................... A61M 11/06 |
| | | | | 128/200.14 |

(Continued)

FOREIGN PATENT DOCUMENTS

| CN | 201283082 Y | 8/2009 |
| EP | 2143411 A1 | 1/2010 |

(Continued)

OTHER PUBLICATIONS

Notification of Transmittal of the International Preliminary Report on Patentability for International Application No. PCT/GR2014/000020 date of mailing Mar. 6, 2015,by the EPO, Munich, Germany.

(Continued)

*Primary Examiner* — Edelmira Bosques
(74) *Attorney, Agent, or Firm* — Peter B. Scull; Hamilton, DeSanctis & Cha LLP

(57) ABSTRACT

For the treatment of the upper respiratory system is used sea water due to its due to its anaplastic, healing and hypertonic (osmosis) characteristics, deriving if it stays for adequate time inside the nasal conchas and nose cavities. This invention for its accomplishment, guarantees a stable column of water for adequate period of time in the nasal cavities and by the ingestion (Valsava) the water is pushed in the nasal conchas and the ducts of the nose sinuses and cavities and is consisted of Central storehouses (1) having a movable pin (4) with manually-operated provides water via the pipe (5) in the mouth (8). The central pipe (5*a*) provides the water to the nose and the small pipe (5*b*) to the periphery of the mouth (8) that expands it for its sealed application and is based in two edges (10). Alternatively the pipes (5) and the mouths are joined by one (5*c*) which is adapted in the (Continued)

Figure 1:
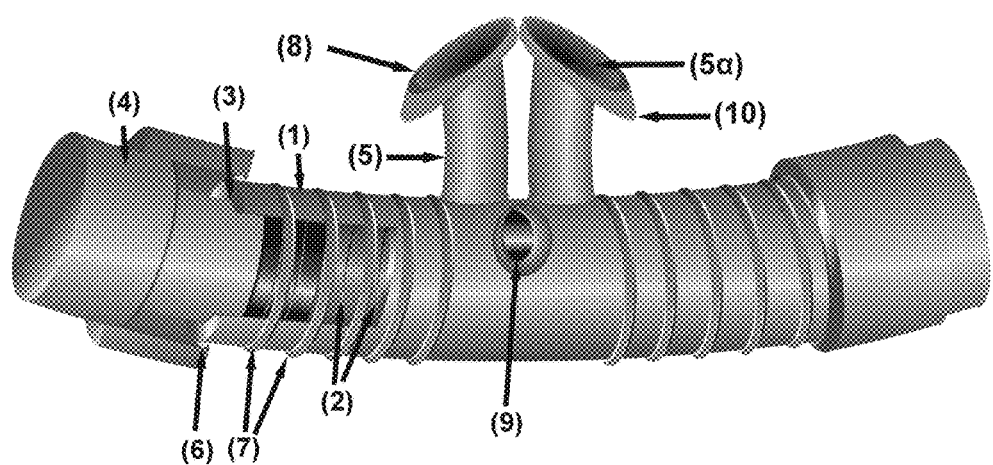

entrance (12) of the bag (1a) with a pin (13), moved by electricity (13) or manually-operated.

12 Claims, 2 Drawing Sheets

(51) Int. Cl.
  *A61H 35/04* (2006.01)
  *A61M 16/06* (2006.01)
  *A61M 3/02* (2006.01)
  *A61H 33/04* (2006.01)
(52) U.S. Cl.
  CPC ... *A61M 16/0666* (2013.01); *A61H 2033/048* (2013.01); *A61M 2210/0618* (2013.01); *A61M 2210/0681* (2013.01)
(58) Field of Classification Search
  USPC .................................................. 604/94.01
  See application file for complete search history.

(56) References Cited

U.S. PATENT DOCUMENTS

| | | | |
|---|---|---|---|
| 8,298,182 | B2 | 10/2012 | Abate et al. |
| 2008/0047559 | A1 | 2/2008 | Fiori |
| 2011/0040250 | A1 | 2/2011 | Abate et al. |
| 2011/0087174 | A1* | 4/2011 | Carpenter ........... A61M 3/0262 604/257 |
| 2011/0301569 | A1 | 12/2011 | Dyer |

FOREIGN PATENT DOCUMENTS

| | | | |
|---|---|---|---|
| EP | 2389918 | A1 | 11/2011 |
| FR | 2297032 | A1 | 8/1976 |
| GB | 125967 | A | 10/1919 |
| GB | 2395129 | A | 5/2004 |
| WO | 8905163 | A1 | 6/1989 |
| WO | 03041780 | A2 | 5/2003 |
| WO | WO2010056491 | A2 | 5/2010 |

OTHER PUBLICATIONS

International Search Report and Written Opinion of the International Searching Authority for PCT/GR2014000020 date of mailing Jul. 14, 2014, 9 pages, by the EPO, (International Search Report from EPO Rijswijk, NL, Written Opinion from EPO Munich, DE). Reply to the Written Opinion of the International Searching Authority for PCT/GR2014000020 date of mailing Jan. 26, 2015, 30 pages, by applicant.

* cited by examiner

DEVICE OF CONTROLLED PROVISION OF SEA WATER IN THE NOSE

The invention relates to a device of controlled and repeated provision of a column of fixed volume sea water in the nasal cavities and the nasal conchas for the reassurance of the osmosis function and valsava exercise. It is used for the disinfection of nasal cavities, the prevention of infections and the treatment of chronic diseases, the cavities of cranium visceral and the upper respiratory system except from influenzas.

It is known from worldwide medical practice that for the treatment of the disorders of the upper respiratory and mainly the cranium visceral (supramaxillary hiatus, frontal sinus, cribrose cells, wedge-shaped sinus, nasal cavities, pharynx) is used the sea water due to its anaplastic, healing and hypertonic characteristics.

Sea water by suitable use, relieves from nasal irritation and sets up its normal function by its anti-pro-inflammatory and cell regenerative characteristic, with are superior from those of normal saline.

For the understanding of the utility of the sea in our organism, we should know its characteristics and its action.

Sea water, as it is known, it is hypertonic due to the increased content of NaCl (9 g/l) as well as of more than 80 minerals and trace elements, including calcium, magnesium, iron, copper, manganese, zinc and others, a composition that gives great osmotic ability and important nutritional and healing value.

The phenomenon of osmosis as well as the nutritional and healing action in order to give the desirable benefits, necessarily need the contact of the hypertonic sea water with the mucosa of the ducts or the sinuses of the nose for a sufficient period of time of stable application. This is achieved by stable, continuous and normal increase of the pressure of the water with an automate and natural way of valsava exercise with the ingestion with closed nostrils.

The valsava test is a method of expiration through the nose with close nostrils and is applied for the dealing of arrhythmias or the equalization of atmospheric pressure of the tympanic membrane. By this exercise pressure is applied towards the nose canals and nose cavities.

Currently, sea water is used for lavage of the nose cavities with simple cleaning devices by spraying or continuous flow and follows the direct absorption of the water, such as the devices with characteristics EP 21143411 A1, application number 09008636,4 & US 2011/0040250 A1, Feb. 17, 2011 & WO 2010/056491 A2, 20 May 2010. By this way of use, the time given is not enough, as well as the necessary pressure of fixed column of water and the impulsion with Valsava movement, in order the water to enter in nasal canals and the ducts of the nasal cavities and the osmotic phenomenon to take place, and therefore the healing result is lost. This fact constitutes a vacancy in existing medical practice, worldwide, that the present invention comes to fulfill.

For the better understanding of the device and its function, its worth to describe some elements of the physiology and pathology of the upper respiratory system.

The respiratory system is subject to continuous risks of viral diseases and microbial infections, mainly in winter.

The respiratory system is armed with various systems of protection, among which is the mucosa of nasal cavities, that constitute the main respiratory route and the filter of the inhaled air from various suspended particulars and microorganisms.

Simultaneously the nasal cavity consists of a nest of prevalence of populations of viruses and microbes for a very large period throughout the entire year, mainly in winter, that constitute mainly the cause of the development of various infections of the upper and lower respiratory system, namely of the nose sinuses and more specifically of the supramaxillary hiatus.

These infections usually conclude to a sub-acute form with mild signs from the nasal cavity and often acquire the characteristics of chronicity and as a result they turn to new resources of microbes carriers and infections.

This phenomenon concerns all ages but mainly younger people and especially children.

By this way the nasal cavities and nasal sinuses from protection bodies of the respiratory system turn to nests of small or greater infections.

The mucosa of the nasal sinuses is subject to disorders such as edema, fattening, dryness, hyperemia, hypertrophy and the free passage and cleaning of the inhaled air is obstacle.

The problem becomes even worse by the encumbrance of the environment mainly of urban centers, the dryness of the air of residences (air conditions, heating bodies etc) that results to further decay of the mucosa, the dehydration of the excretums adjusted in the surface of the endothelium and therefore obstacle the natural air ducts, the excretum of the nose sinuses to be channeled with difficulty and the free passage of air to be impeded.

The structural and operational disorders of the cranium visceral in combination with the encumbrance of the mucosa of the air ducts of the oral part of the pharynx, trachea and bronchus due to encumbered environmental conditions, decrease the defensive ability and form the suitable ground for easier development of infections, more specifically when the organism is exposed to adverse conditions of cold, extreme fatigue, unrest, abuses etc So the maintenance of clear and healthy nasal cavities and nasal sinuses of human beings must constitutes a medical, family and personal care. Continuous systematic researches of the international medical community form recommendations of hygiene living conditions and treatments, aiming to the support of the immunologic ability of the organism and the prevention of infections of the upper and lower respiratory system.

The nursing and care of the hygiene of the upper respiratory system and mainly of the nasal cavity and the nose sinuses targets on the hand to the maintenance of a healthy mucosa and the disinfection of the cavities and on the other hand on its sanitation, when chronic disorder and decay exists.

For the accomplishment of this target are used various preparations of topical use among which sea water.

Useful information for the benefits and the time of application of the sea are taken from the bathers using swimming masks for 30 to 60 minutes.

During swimming with masks the nasal bags of the mask is filled with water that fills the nasal cavities that stay filed during the time of swimming. Part of that water with hydrostatic external pressure aid that the bag of the masks has, comes to the nose sinuses and from time to time is removed by periodic ingestion of the swimmer, and therefore the nasal cavities, the oral part of the pharynx and the mouth of the Eustachian channels are cleared.

During ingestion with close nostrils as in swimming with mask, the elevation of the soft palate for the isolation of the oral part of the pharynx from the moth pharynx, opens the Eustachian channels and presses the water to the nasal ducts, where the excretory ducts of nose sinuses discharge, by forming a variation of the automate Valsava exercise.

By the pressure enforced with the ingestion's movements of the soft palate, the water is gradually pushed inside the ducts and mainly via the sinus foremen the supramaxillary hiatus is filled.

It is obvious that during the swimming where the sanal cavity and ducts remain full with a stable column of sea water under pressure, is offered a sufficient and necessary period for the hypertonic characteristic of water to function in order the osmotic phenomenon to be developed and by the assistance of the movements of Valsava exercise the mucosa of renal cavities and nose sinuses to be cleared.

At the end of swimming we remark that for a long lasting period even more than an hour, is aborted from the nose of the swimmer a large quantity of fluid, semi-fluid up to high viscosity white, off white or yellow green fluids.

Those excretions derive either from the mucosa of the nasal cavity and the nose conchas or by the nose sinuses, which by osmosis and cleaning were removed from those cavities and cleaned those ducts and the excretory ducts. By this way the relevant mucosa is renewed.

In accordance with the above mentioned remarks we elaborated an epidemic research in 402 swimmers users of masks (is attached) wherefrom important information were gathered for the statistically important profitable affect of the sea provided that the nasal cavities remain full of a stable column of water for more than 30 minutes.

Driven by the above mentioned scientific remarks we proceeded to the manufacture of a device that reassures the above mentioned preconditions of stable sea water column under pressure, for the continuous fracture of the nostrils for the complete development of the osmpotic phenomenon as well as of the Valsava movement.

By the present application a variation of Valsava exercise is succeeded. Valsava movement increases the air pressure in the whole cavity of the upper respiratory when trying to expire with closed mouth and nostrils. Valsava exercise, as well as its variant, where human swallows with his nose closed, is applied for the known equalization of the airplane travelers, and this is why chewing gum is suggested during the flight. When using the proposed device, the outer ducts of nostrils are totally closed and the gentle pressure of the two storehouses pushes gently and without any pain their contents, which are either sea water or saline containing antibiotics, towards the nasal cavities. When the cavities are filled, then the liquid moves backwards to the epipharynx and the swallowing reflex is automatically generated. For the swallowing to happen the soft palate is elevated and pushes the sea water or saline containing antibiotic towards the nostrils exit. Since the nostrils are closed by the device, the content water is pressed and finds an outlet through the nasal concha and the foramens (apertures) of the excretory ducts of paranasal sinus, gradually enters in the sinus and the therapeutic result is achieved.

The device has:

1) A main storage area (1) also known as and/or comprising two serial tubular central storehouses (1), of four departments (2) each, with 2 or 3 or 4 cc of sea water in each department (infantile's—children's—juveniles'). In the outer end (3) each storehouse has a movable pin (4) which with every simple pressure with the fingers of the hands provides to the pipe (5) the content of each department namely 2-4 cc of water. Each stage of promotion of the pin is guided by a trolling pin (6) that moves on a interruptible driver (7).

2) Each tubular storehouse has a channel pipe (5) that ends in an edge with mouth (8) The main channel or main pipe (5a) also known as the central channel (5a) provides the water of the tubular storehouse to the nose while the small pipe (5b) also known as the secondary channel (5b) transfers the water of the small storehouse (9) which is also known as a secondary storehouse (9) and which is disposed between the pipes (5), to the periphery of the mouth (8) which expands for the elevation of the wing of the nose and the sealed application for the facilitation of the water's entrance that fills the nasal cavity and the nasal conchas.

3) The mouth (8) has the anatomic shape of the exit of the nasal cavity in order to achieve sealed application when the periphery of the mouth (8) is expanding. It has two points (10) out frontal and out lower, so the mouth to be impacted and based in the last upper-out and lower-out notch (11) of the exit of the nasal cavity.

4) The device in an alternative choice has as follows: Two channel pipes (5) which by their mouths (8) are joined in one pipe (5c). At the confluence of the channel pipes there is a small storehouse (9a) that expands the periphery of the mouths (8). The pipe (5c) ends and is adopted in an entrance (12) in a bag (1a) of sufficient content of sea water for many therapeutic uses, that bears in its base a pin (13). The pin is moved by a thin mechanism supplied from a battery of 12 volt (14) and is activated by simple pressure of a surface switch (15) providing in every movement 4, 6, 8 cc of water to the nostrils. In the alternative choice of this application the bag (1a) is of multiple use, from other users too, by the ability of refilling of the sea water and the pipe (5c) is a personal consumable spare part of few uses.

By this application we achieve a prolonged stay of the hypertonic water in nasal cavities and nasal conchas and therefore a hypertonic environment is formed in touch with the excretory routes of the supramaxillary hiatus and the front and other nose sinuses.

This invention offers the ability to provide 2-4 cc of water for each nasal cavity by the application of a mild pressure every 10-20 minutes of an hour. The application of the therapy of total duration 30 to 60 minutes respectively to the case is competent for the accomplishment of the target.

By each simple pressure of the device a new column of clean water is promoted for the maintenance of the power of the osmotic phenomenon, whereas simultaneously the old column is pushed to the oral part of the pharynx and cleans its mucosa as well as the mouths of the Eustachian channels and then by the movement of ingestion is aborted from the mouth. Simultaneously to the ingesting movement with the elevation of the soft palate a new column of water is pushed towards the nasal ducts (Valsava movement) for the continuance of the treatment.

By this way each user may in his/her living room or office, easily, painless to achieve the cleaning, disinfection and revitalization of the cavities of the upper respiratory system, one or more times per week and to enjoy the benefits of the sea and the prevention of the health of his/her respiratory system.

The proposed therapy:

To chronic infections of the upper respiratory system are required 1-3 applications per day till the complete cure of the disease For health prevention are required 1-2 applications per week The Figures that follow describe the device for the best understanding of the reader:

FIG. 1: The entire device and its parts

Figure 2:
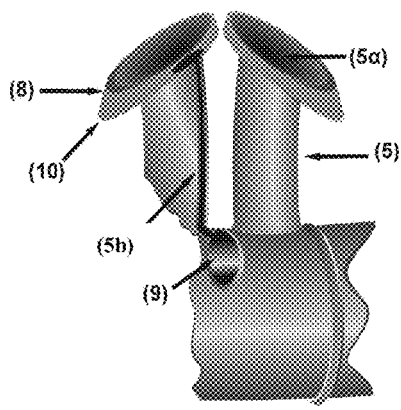

FIG. 2: Enlargement of the pipes 5a and 5b

Figure 3:
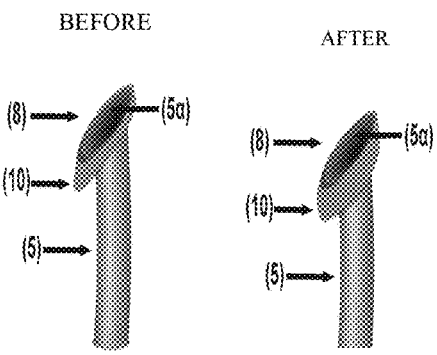
Figure 4:
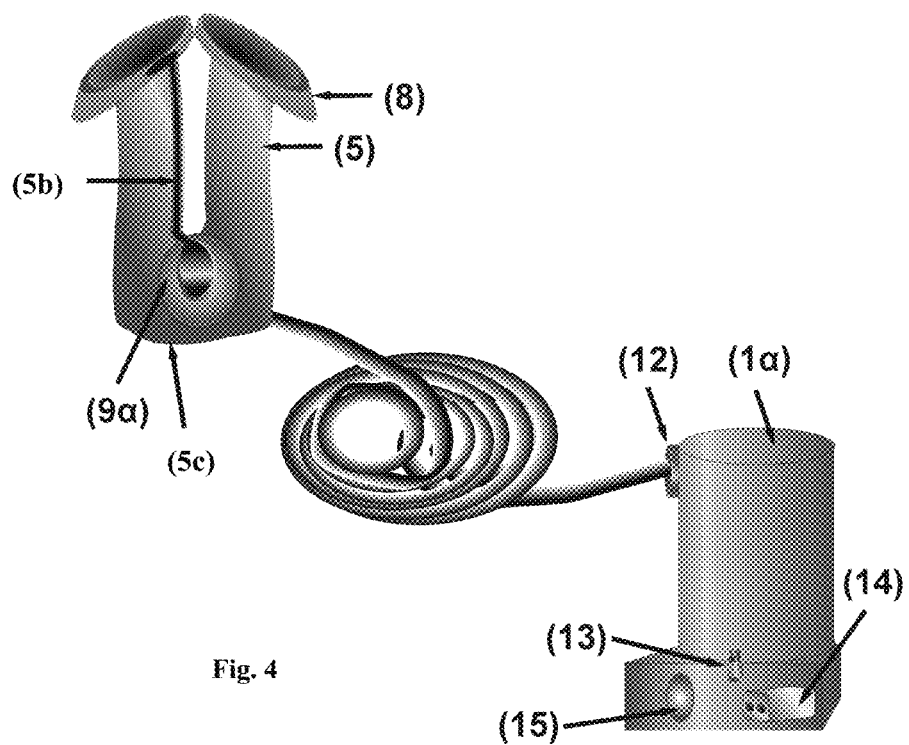

FIG. 3: The expansion of the outer periphery of the mouth
FIG. 4: Schematic description of the alternative device.

The invention claimed is:

1. A device to simultaneously provide, in a controlled and repeated manner, a quantity of fixed volume of sea water or saline into nasal cavities, nasal conchae and paranasal sinuses of both nostrils of a nose, comprising:
   a base having at least
      a main storage area and
      a small storehouse; and
   two pipes, connected to the base,
   each of the two pipes having:
      a main channel and
      a secondary channel, and
      a mouth at one end thereof;
         the main and secondary channels connecting at the one end with the mouth;
         the mouth having an expandable periphery,
         wherein the respective main channels are connected to the main storage area which is configured to simultaneously provide, upon activation of a mechanism, content to the main channels from the main storage area,
         wherein a first of the main channels is configured to provide content to a first nostril and a second of the main channels is configured to simultaneously provide content to a second nostril and
         wherein the small storehouse is configured to be filled with water and provide water through the respective secondary channels to each of the peripheries of each of the mouths to expand each of the peripheries of each of the mouths.

2. The device according to claim 1, where the mouth has a shape to achieve sealed application when the periphery expands and wherein each mouth has two points one out frontal point and one out lower point.

3. The device according to claim 1, wherein the base comprises the main storage area in the form of two tubular storehouses, wherein one is connected to the main channel of one pipe and the other to the main channel of the other pipe, respectively, and configured to provide content to both main channels upon pressure.

4. The device according to the claim 3, where each tubular storehouse has connected departments and a movable piston at an outer end which is configured, by a simple pressure with the fingers of a hand, to provide to the main channel the content of each department, respectively, and where the departments are separated externally with interruptible drivers.

5. The device according to the claim 3, wherein each tubular storehouse comprises four departments.

6. The device according to the claim 1, wherein the two main channels are joined in one common pipe at the base and wherein the common pipe is configured to be connected to and receive content from a multiple use main storage area.

7. The device according to claim 6, further comprising the multiple use main storage area.

8. The device according to claim 7, wherein the multiple use main storage area comprises:
   a base with a piston;
   a mechanism for moving the piston;
   wherein, upon activation of the mechanism the device is configured to provide a preselected quantity of content to both nostrils.

9. The device according to claim 8, wherein the mechanism is manual operated and each time provides the preselected quantity to both nostrils.

10. The device according to claim 8, wherein the device comprises a battery for providing power to the mechanism and the multiple use main storage area further comprises a surface switch, connected between the battery and the mechanism, for activating the mechanism.

11. The device according to claim 1, wherein the main storage area comprises sea water.

12. The device according to claim 1, wherein the main storage area comprises saline containing antibiotic.

* * * * *